United States Patent [19]

Sherman et al.

[11] Patent Number: 5,120,552
[45] Date of Patent: Jun. 9, 1992

[54] ENZYMATIC TREATMENT OF PRODUCE CELL WALL FRAGMENTS

[75] Inventors: Mark Sherman, Elgin, Ill.; Michelle A. Mrozik, Roseville, Minn.

[73] Assignee: The Pillsbury Company, Minneapolis, Minn.

[21] Appl. No.: 800,685

[22] Filed: Dec. 2, 1991

Related U.S. Application Data

[63] Continuation of Ser. No. 647,952, Jan. 30, 1991, abandoned.

[51] Int. Cl.$^5$ .............................................. A23L 1/212
[52] U.S. Cl. ........................................ 426/50; 426/52
[58] Field of Search ................................... 426/50, 52

[56] References Cited

U.S. PATENT DOCUMENTS

| | | | |
|---|---|---|---|
| 4,214,007 | 7/1980 | Hase et al. | 426/44 |
| 4,284,651 | 8/1981 | Bruemmer | 426/50 |
| 4,333,955 | 6/1982 | Murata et al. | 426/44 |
| 5,000,967 | 3/1991 | Adams | 426/50 |

OTHER PUBLICATIONS

P. Bogh, "When Less is More", Prepared Foods, Aug. 1990; pp. 138-140.
Anon, "Vacuum Cleaned Fresh Citrus", Citrogaph, vol. 74, No. 8 Jun. 1989; pp. 203-204.
S. Adams, "A-Peeling New Citrus Technology", Agricultural Research, Jan. 1989; pp. 8-9.
Y. Tatsumi, Scanning Electron Microscopy of Carrot Stick Surface to Determine Cause of White Translucent Appearance.

Primary Examiner—Arthur L. Corbin
Attorney, Agent, or Firm—Fredrikson & Byron

[57] ABSTRACT

A method for improving the desirable aesthetic appearance and quality of fruit and vegetable produce, which has been cut or peeled to expose an interior surface having cell wall fragments, that would otherwise be diminished due to the presence of cell wall fragments, is provided by treating the cut or peeled produce in an enzyme solution. The enzyme treatment selectively removes substantially all cell wall fragments from the interior surface of the produce. The enzyme treatment also substantially extends the shelf-purchase life of the produce.

27 Claims, 1 Drawing Sheet

ENZYMATIC TREATMENT OF PRODUCE CELL WALL FRAGMENTS

This application is a continuation of application Ser. No. 07/647,952, filed Jan. 30, 1991, now abandoned.

BACKGROUND OF THE INVENTION

The present invention is directed to fruit and vegetable produce. More specifically, the present invention is directed toward an enzymatic method of improving the aesthetic appearance of produce which has been cut or peeled. The present invention is further directed to prolonging the shelf-purchase life of produce which has been cut or peeled.

The newly exposed surfaces of many articles of produce are subject to dehydration within a short period of time after being exposed. The surface of produce may be exposed by cutting, peeling or a combination thereof. Often times, the peeled surface of produce is affected to a greater extent because of the usually larger surface areas involved. Specifically, the entire surface of peeled produce is subject to dehydration rather than solely the cut edge. The dehydration manifests itself as a whitening of the produce at the cut edge or peeled surface which has been exposed. The problem is most pronounced on produce that has been abrasively peeled. Consumers tend to associate this appearance with aged or non-fresh produce. Hence, the dehydration problem significantly reduces the aesthetic appearance, quality, and more importantly, the shelf-purchase life of the produce.

A paper presented by Tatsumi at the 1989 annual meeting of the American Society of Horticultural Sciences suggests that the dehydration is caused by the presence of cell wall fragments that occur on the cut surfaces of vegetables. Scanning Electron Microscopy (SEM) was used by Tatsumi to verify the presence of these cell wall fragments on cut produce. The cell wall fragments appear to be caused by the mechanical shearing forces created by a knife as it cuts the vegetable. This paper did not examine peeled vegetables, but it is very likely that similar mechanical forces are responsible for the dehydration seen in this method of processing produce.

SEM investigation of produce items that have either been cut or peeled reveal the presence of cell wall fragments on the newly exposed surfaces Tatsumi suggested using razor blades instead of knives to cut the produce as a remedy for the dehydration problem since the razor sharp blade would leave a less fragmented edge than would a knife. However this approach is not practical for cutting produce on a commercial scale since the produce is handled by mechanical cutters. Also, Tatsumi did not propose any solution to the dehydration problem on the surfaces of produce which have been exposed by peeling.

Bruemmer (U.S. Pat. No. 4,284,651) discloses the use of mixtures of cellulase and pectinase to dissolve the albedo of citrus fruit in order to facilitate peeling. Albedo is the sticky white tissue between the rind and the juice sections of citrus fruit The thick peel of the citrus fruit is first carefully scored so as to penetrate the albedo while not cutting into the juice sections The enzyme mixture is then vacuum infused into the albedo and allowed to react for a period of time. After sufficient incubation, the peel nearly falls off of the otherwise intact citrus fruit which is then washed and packaged prior to being stored in refrigeration.

Hase (U.S. Pat. No. 4,214,007) and Murata (U.S. Pat. No. 4,333,955) disclose a method of processing dried beans as instant food. One of the steps in processing the raw beans is an enzymatic treatment with cellulase or a mixture of cellulase and pectinase. The treatment serves to partially destroy the cell wall of the beans. The beans, once processed, are capable of being instantly reconstituted to an edible condition with the addition of boiling water. The enzyme treatment is cited as increasing the beans' permeability to the boiling water when the beans are being reconstituted for consumption.

Guigou (French Pat. No. 2,207,657) discloses the use of a commercially available enzyme preparation which contains various pectinases and cellulases to eliminate the peel or skin of fruits and vegetables by enzymatic hydrolysis. The enzyme is deactivated during the pasteurization step in the processing of the fruit or vegetable. The enzyme treatment is cited as increasing throughput while reducing labor input and decreasing waste generated by traditional methods of peeling.

At present, no one has attempted to rectify the problem of produce dehydration in a manner similar to that of the present invention. The only related use of enzymes in food processing to date has involved destroying the structural integrity of the cell wall so it was indeed surprising when it was discovered that cell wall fragments could be selectively digested, leaving intact cell walls unaffected. The present invention offers a quick, easy, and inexpensive process for improving the appearance and quality of produce that has been cut or peeled while also significantly prolonging its shelf-purchase life.

SUMMARY OF THE INVENTION

The desirable aesthetic appearance of produce which has been cut or peeled, that would otherwise be diminished due to the presence of cell wall fragments, is preserved by treating the produce in an enzyme solution The enzyme treatment also greatly increases the shelf-purchase life of the treated produce. The process comprises the steps of soaking the produce which has been cut or peeled in an enzyme solution, draining the enzyme solution off of the produce, rinsing the produce with water, denaturing any enzyme residual still adhering to the produce in an alkaline solution, rinsing the treated produce with water and storing the treated produce in refrigeration.

DETAILED DESCRIPTION

For purposes of this invention, cutting or peeling of the produce may be accomplished by any suitable means. Examples of such cutting or peeling means would include, but not be limited to, mechanical cutters, human workers or abrasive peelers. Examples of such cut produce pieces or peeled produce items would include carrot coins, apple wedges, celery stalks, peeled baby carrots and the like.

Figure 1:
FIG. 1 depicts an abrasively peeled baby carrot that was not enzyme treated, i.e. conventionally processed.
Figure 1A:
FIG. 1a shows an enlarged view of the produce surface.
Figure 2:
FIG. 2 depicts an abrasively peeled baby carrot that was enzyme treated.
Figure 2A:
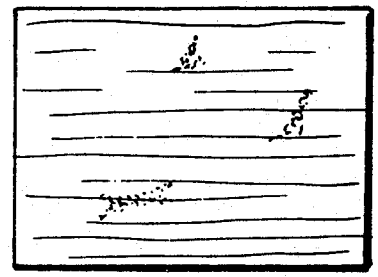
FIG. 2a shows an enlarged view of the produce surface.

The aesthetic appearance of produce is improved by the enzyme treatment of the present invention in the following manner. Abrasively peeled carrots, for example, display a whitish, hair-like texture when stored in refrigeration after processing by conventional methods as a result of dehydration due to the presence of cell wall fragments FIG. 1 depicts an abrasively peeled baby carrot that has been conventionally processed The color quality of conventionally processed carrots also progressively decreases with the duration of storage. Specifically, the natural orange color of the carrot takes on a yellowish cast in addition to the development of the whitish, hair-like texture. Carrots which have undergone the enzyme treatment retain an appetizing orange color even after extended refrigerated storage Carrots treated by means of the present invention are also substantially free of the hair-like texture which greatly reduces the aesthetic appearance of conventionally processed produce. FIG. 2 depicts an abrasively peeled baby carrot that has undergone the enzyme treatment.

The shelf-purchase life of produce treated by the present invention at the outset is extended in two related ways. First, the consumer is likely to express a purchase preference for enzyme treated produce over conventionally processed produce of the same age because of the improved aesthetic appearance. Second, the grocer will keep the enzyme treated produce on the shelves for longer periods of time than conventionally processed produce of the same age because of its continued fresh appearance and consumer willingness to purchase it. It is important to note that enzyme treated produce of the present invention continues to be safe for human consumption even after storage periods of a duration which would result in the disposal of conventionally processed produce of the same age. It is further important to note that the decision which results in the disposal of most produce is based on a visual assessment that it is no longer fit for consumption. Often, this assessment is based solely upon the aesthetic appearance of the produce when in fact, it is still quite edible and generally needs only to be washed or re-peeled. This practice constitutes waste and is prevalent both in grocery stores and in the home.

The treatment is also equally effective in substantially improving the aesthetic appearance and extending the shelf-purchase life of produce which conventionally would be considered aged. For example, produce which displays an unappetizing aesthetic appearance because of dehydration and discoloration may be "cleaned up" as a result of the enzyme process. This clean-up could optionally include the re-washing and re-peeling of the produce prior to subjecting it to the enzyme treatment. The restoration of an appetizing aesthetic appearance would significantly extend the shelf-purchase life of produce which would otherwise be discarded. When produce has not been subjected to the enzyme treatment at the outset, treatment of aged produce at this stage is effective in extending the shelf-purchase life to a point beyond which conventionally processed produce would never reach. The overall actual and perceived quality of the produce is greatly increased by the combination of improved aesthetic appearance and extended shelf-purchase life.

In the practice of the present invention, produce is cut into convenient shapes and sizes by any suitable means. Peeled produce may also be used if desired. Of course, produce may be peeled and cut sequentially or simultaneously for purposes of this invention. The cut produce pieces or peeled produce items are first placed in a hopper containing a dilute enzyme solution and allowed to soak. Any of a number of commercially available cellulases or pectinases are suitable for the objectives of the present invention. Most commercially available enzyme preparations that are labeled as cellulases or pectinases are in fact mixtures of various specific enzymes which display a preference for a particular substrate.

Since the produce is intended for human consumption, generally only those preparations that are Generally Recognized As Safe (GRAS) are used in the process. Of course, any number of enzyme preparations that are not GRAS would be suitable for use in the treatment if the produce was not intended for human consumption.

The enzyme solution is maintained at a buffered pH of between 4 and 7.5, preferably pH=5.4. The optimal duration of the treatment period in the enzyme solution for each particular type of produce can be calculated. The temperature of the enzyme solution plays a significant role in dictating the duration of the treatment period at any given incubation temperature. The manner of processing the produce prior to the enzyme treatment must also be taken into account. For example, carrot coins and abrasively peeled carrots, although examples of the same vegetable, require dissimilar treatment periods at the same incubation temperature to achieve full benefit of the invention because of the their differences in size, shape and surface area. These differences translate into differing quantities of cell wall fragments, hence treatment periods of differing duration. Peeled produce items generally require a longer incubation period than do cut produce pieces. The produce may be gently agitated during the enzyme treatment to facilitate access of the enzyme to the entire surface of the produce.

The enzyme treatment has been found effective when conducted within a temperature range of between 34F and 140F. Generally however, the enzyme treatment is carried out at room temperature. Specific elevated temperatures, which are enzyme selection dependent, within the effective range would of course take advantage of generally increasing enzyme activity as a function of increasing temperature. The treatment may even be less effectively conducted at temperatures below room temperature. Accordingly, the selected incubation temperature of the enzyme solution figures prominently in the calculation of the optimal duration of the treatment period. For example, peeled baby carrots may only require a 30 minute treatment period when the incubation temperature is 120F, but may require up to 3 hours if the incubation temperature is 72F. Also, the enzyme concentration may me manipulated in order to shorten the treatment period at any given incubation temperature simply by the addition of surplus enzyme. Accordingly, standard principals of enzyme kinetics such as temperature, concentration, pH, etc. may be manipulated in order to expedite the process. Bearing in mind the commercial implementation concerns of cost, complexity and throughput of the process, an optimal treatment may not be the most expeditious.

After a sufficient treatment period under suitable conditions, the enzyme solution is drained off of the produce. The enzyme solution is not discarded, but rather it is ultrafiltered to be recycled in the process. The enzyme concentration of the solution is monitored regularly and any adjustment in the concentration back to the optimal point is accomplished by the addition of new enzyme. Optionally, the enzyme solution may contain a dilute concentration of chlorine or other suitable agent to prohibit microbial growth.

After draining off the enzyme solution, the produce is washed with water. Agitation may accompany this washing. The wash serves to remove as much as possible any of the enzyme solution that may still be adhering to the produce. Any enzyme residual remaining after the wash is denatured in the next step in the process. The washed produce is submerged in an alkaline solution The optimal pH for this solution is between 8 and 12, preferably pH=10. Generally, the exposure to the alkaline solution is less than a minute Once again agitation may be used to facilitate access by the alkaline solution to the entire wetted surface of the produce. After sufficient exposure to the alkaline solution to guarantee complete denaturation of any remaining enzyme, the alkaline solution is drained off.

After the denaturation step, the produce is thoroughly rinsed with water to remove any residue of the alkaline solution which may adhere to the produce. Gentle agitation may also accompany the rinsing of the produce. The produce is next dewatered by means of a centrifuge-type drum which removes the excess water remaining after the final rinsing. The product may be dewatered by any suitable means which would not in any way diminish the aesthetic appearance or quality of the produce.

When the process is complete, the produce is sorted and packaged according to standard practices Once packaged, the produce is stored and distributed under refrigeration. The treated produce is ideal for distribution to both the retail and institutional markets.

The invention may be more fully understood by reference to the following examples The examples are illustrative in nature and not intended to be limiting in any manner.

EXAMPLE 1

The following Table represents a sample of the enzymes that have proven effective for purposes of this invention.

TABLE 1

| Enzyme | Concentration |
|---|---|
| Cytolase CL[1] | 500-1400 ppm |
| Cytolase M102[1] | 800-1600 ppm |
| Pectinol HS[1] | 2600-4000 ppm |
| Rohament K[2] | 3500-4600 ppm |
| Enzyco Pectinase[3] | 8200-9800 ppm |
| Biopectinase S.S.[4] | 9800-11000 ppm |

[1]Genencor, Inc. 180 Kimball Way, South San Francisco, CA 94080
[2]Rohm Tech, Inc. 195 Canal Street, Malden, MA 02148
[3]Enzyme Development Corp. 2 Penn Plaza. Suite 2439, New York, NY 10121-0034
[4]Biocon 1833 57th Street, Sarasota, FL 34243

The concentration of the enzyme is calculated to be effective on a 1 pound sample of carrots at room temperature.

A 1 pound sample of carrot coins was incubated at room temperature for 2-3 hours in a buffered solution (pH=5.4) of Cytolase CL with an enzyme concentration of 800 ppm. At the end of the treatment period, the enzyme solution was drained off of the carrot coins which were then washed with water. The enzyme solution was ultrafiltered and recycled for use in the process. The enzyme concentration was checked and any adjustment was performed. The carrot coins were then immersed in a alkaline solution with a pH=10 for approximately 30 seconds. After the enzyme residual was denatured by the alkaline solution, the carrots were once again washed with water. The carrot coins were then dewatered by means of a centrifuge-type drum. Optionally, agitation may accompany all the steps in the process with the exception of the drying.

EXAMPLE 2

This example was performed exactly as Example 1 with the exception that a 1 pound sample of abrasively peeled baby carrots was incubated at 120 F for 30 minutes in a buffered enzyme solution (pH=5.4) of Rohamnet K with a concentration of 3500 ppm.

What is claimed is:

1. A method for substantially improving the aesthetic appearance and shelf-purchase life of produce which has been mechanically cut or peeled to expose an interior surface of the produce having cell wall fragments subject to dehydration, comprising: treating said produce in an enzyme solution under suitable conditions for a sufficient treatment period to remove the cell wall fragments from the exposed interior surface to the extent necessary to achieve said improved aesthetic appearance and shelf-purchase life.

2. The method of claim 1, wherein substantially all cell wall fragments are selectively removed.

3. The method of claim 1, further comprising draining said enzyme solution off of said produce at the completion of said sufficient treatment period.

4. The method of claim 3, further comprising rinsing said produce with water after draining off said enzyme solution.

5. The method of claim 4, further comprising denaturing by exposure to an alkaline solution for a sufficient time any residual of said enzyme solution still adhering to the surface of said produce after said rinsing with water.

6. The method of claim 5, further comprising draining said alkaline solution off of said produce after said denaturing of said enzyme residual.

7. The method of claim 6, further comprising rinsing said produce with water after draining off said alkaline solution.

8. The method of claim 7, further comprising dewatering said produce after the second of said rinses with water.

9. The method of claim 5, wherein said alkaline solution is maintained at a pH of between 8 and 12.

10. The method of claim 9, wherein the pH of said alkaline solution is 10.

11. The method of claim 3, wherein said enzyme solution is ultrafiltered and recycled after being drained off of said produce.

12. The method of claim 11, wherein additional enzyme is added to said ultrafiltered enzyme solution to maintain the enzyme concentration at optimal levels.

13. The method of claim 1, wherein said enzyme solution is buffered to a pH of between 4 and 7.5.

14. The method of claim 13, wherein the pH of said enzyme solution is 5.4.

15. The method of claim 1, wherein the said enzyme solution is maintained at a temperature of 34-140F.

16. The method of claim 1, wherein said enzyme solution contains pectinase.

17. The method of claim 1, wherein said enzyme solution contains cellulase.

18. The method of claim 1, wherein said enzyme solution contains a mixture of pectinase and cellulase.

19. A method for substantially improving the quality of produce comprising mechanically cutting or peeling the produce to expose an interior surface of the produce having cell wall fragments resulting from such cutting or peeling which are subject to dehydration and then:
(a) treating said produce for a sufficient period of time in an enzyme solution under suitable conditions to remove cell wall fragments to the extent necessary to achieve said improved quality;
(b) draining said enzyme solution off of said produce at the completion of said sufficient period of time under said suitable conditions:
(c) rinsing said produce with water after draining off said enzyme solution;
(d) denaturing any enzyme residual still adhering to the surface of said produce by exposure to an alkaline solution for a sufficient length of time;
(e) draining said alkaline solution off of said produce after said denaturing of said enzyme residual;
(f) rinsing said produce with water after draining off said alkaline solution; and
(g) dewatering said produce after the second of said rinses with water.

20. The method of claim 19, wherein substantially all cell wall fragments are selectively removed.

21. The method of claim 19, wherein said enzyme solution is buffered to a pH of between 4 and 7.5.

22. The method of claim 19, wherein said alkaline solution is maintained at a pH of between 8 and 12.

23. The method of claim 19, wherein the temperature of said enzyme solution is 34–140F.

24. The method of claim 19, wherein said enzyme solution contains pectinase.

25. The method of claim 19, wherein said enzyme solution contains cellulase.

26. The method of claim 19, wherein said enzyme solution contains a mixture of pectinase and cellulase.

27. A method for substantially improving the aesthetic appearance and shelf-purchase life of non-citrus produce comprising mechanically cutting or peeling the produce to expose an interior surface of the produce having cell wall fragments resulting from such cutting or peeling which are subject to dehydration, and treating said produce in an enzyme solution under suitable conditions for a sufficient treatment period to remove the cell wall fragments from the exposed interior surface to the extent necessary to achieve said improved aesthetic appearance and shelf-purchase life.

* * * * *